US010089728B2

(12) United States Patent
Nakamura et al.

(10) Patent No.: US 10,089,728 B2
(45) Date of Patent: Oct. 2, 2018

(54) RADIATION-IMAGE PROCESSING DEVICE AND METHOD

(71) Applicant: FUJIFILM Corporation, Tokyo (JP)

(72) Inventors: Keigo Nakamura, Ashigarakami-gun (JP); Tomoyuki Takahashi, Ashigarakami-gun (JP)

(73) Assignee: FUJIFILM Corporation, Minato-Ku, Tokyo (JP)

(*) Notice: Subject to any disclaimer, the term of this patent is extended or adjusted under 35 U.S.C. 154(b) by 107 days.

(21) Appl. No.: 15/001,411

(22) Filed: Jan. 20, 2016

(65) Prior Publication Data

US 2016/0148355 A1   May 26, 2016

Related U.S. Application Data

(63) Continuation of application No. PCT/JP2014/003798, filed on Jul. 17, 2014.

(30) Foreign Application Priority Data

Jul. 23, 2013  (JP) .................................. 2013-152342

(51) Int. Cl.
G06T 5/00 (2006.01)
A61B 6/03 (2006.01)
A61B 6/00 (2006.01)
G06T 7/00 (2017.01)

(52) U.S. Cl.
CPC .............. *G06T 5/008* (2013.01); *A61B 6/032* (2013.01); *A61B 6/4233* (2013.01); *A61B 6/505* (2013.01); *A61B 6/5217* (2013.01); *G06T 7/0012* (2013.01); *A61B 6/542* (2013.01);

(Continued)

(58) Field of Classification Search
CPC combination set(s) only.
See application file for complete search history.

(56) References Cited

U.S. PATENT DOCUMENTS 5,164,993 A     11/1992  Capozzi et al.
5,271,401 A  *  12/1993  Fishman ................ A61B 6/481
                                                                424/9.4

(Continued)

FOREIGN PATENT DOCUMENTS

JP      6-14193 A    1/1994
JP      6-61325 B2   8/1994

(Continued)

OTHER PUBLICATIONS

International Search Report for PCT/JP2014/003798 dated Sep. 16, 2014.

(Continued)

*Primary Examiner* — Tsung-Yin Tsai
(74) *Attorney, Agent, or Firm* — Sughrue Mion, PLLC (57) ABSTRACT

Feature amount calculation unit determines that the diagnosis target is a bone portion of a subject, and calculates a feature amount of a density of the radiation image based on a soft region in a radiation image acquired by irradiating a photographic subject with radiation. An image processing unit performs image processing including gradation processing on the radiation image, such that the feature amount becomes the target density, to acquire a processed radiation image.

10 Claims, 6 Drawing Sheets

(52) U.S. Cl.
CPC ............ *G06T 2207/10116* (2013.01); *G06T 2207/30008* (2013.01)

(56) References Cited

U.S. PATENT DOCUMENTS

| | | | | |
|---|---|---|---|---|
| 6,141,437 A * | 10/2000 | Xu | ........................ | G06T 7/0012 128/922 |
| 2003/0215120 A1* | 11/2003 | Uppaluri | ................ | A61B 6/482 382/128 |
| 2004/0151358 A1* | 8/2004 | Yanagita | ............... | G06F 19/321 382/132 |
| 2005/0135665 A1* | 6/2005 | Shinbata | ................. | G06T 5/004 382/132 |
| 2009/0136110 A1* | 5/2009 | Kaji | ........................ | G06T 5/009 382/132 |
| 2013/0094740 A1 | 4/2013 | Vandenberghe | | |
| 2016/0093025 A1* | 3/2016 | Takahashi | ............... | G06T 5/008 382/132 |
| 2016/0093096 A1* | 3/2016 | Ouji | ..................... | G06K 9/4604 382/131 |

FOREIGN PATENT DOCUMENTS

| | | |
|---|---|---|
| JP | 11-327066 A | 11/1999 |
| JP | 2000-23950 A | 1/2000 |
| JP | 2000-79110 A | 3/2000 |
| JP | 2001-120524 A | 5/2001 |
| JP | 2001-212118 A | 8/2001 |
| JP | 2001-224576 A | 8/2001 |
| JP | 2006-223739 A | 8/2006 |
| JP | 2010-194261 A | 9/2010 |
| JP | 4844560 B2 | 12/2011 |

OTHER PUBLICATIONS

Written Opinion for PCT/JP2014/003798 dated Sep. 16, 2014.
Communication dated Sep. 13, 2016 from the Japanese Patent Office in counterpart application No. 2013-152342.

* cited by examiner

RADIATION-IMAGE PROCESSING DEVICE AND METHOD

CROSS-REFERENCE TO RELATED APPLICATIONS

This application is a Continuation of PCT International Application No. PCT/JP2014/003798 filed on Jul. 17, 2014, which claims priority under 35 U.S.C. § 119(a) to Japanese Patent Application No. 2013-152342 filed on Jul. 23, 2013. Each of the above applications is hereby expressly incorporated by reference, in its entirety, into the present application.

BACKGROUND OF THE INVENTION

1. Field of the Invention

The present invention relates to a radiation-image processing device and method for performing gradation processing on a radiation image.

2. Description of the Related Art

A radiation image used for image diagnosis is acquired through imaging in a computed radiography (CR) system or imaging using a radiation detector (FPD), but a dynamic range of the acquired radiation image is very wide. When an entire dynamic range of the radiation image having a wide dynamic range is converted into an image, a contrast of the image is lowered and is not suitable for diagnosis. Therefore, in order to adjust the dynamic range of the radiation image and obtain an appropriate density and contrast of an image to be displayed, image processing such as gradation processing or frequency enhancement processing is performed. As a scheme of gradation processing, for example, a scheme of obtaining a histogram of pixel values of a radiation image, switching algorithms or parameters based on accessory information such as an imaged portion of the radiation image, an imaging direction, and an age of test substance, generating a portion (main histogram) corresponding to a main region in the histogram, and assigning a gradation curve so that a density range of a main histogram falls within a dynamic range of a display device has been proposed (for example, JP1994-61325B (JP-H06-61325B)). Further, a scheme of setting a region of interest (ROI) in a region for attention on the radiation image, switching algorithms or parameters based on the accessory information of the radiation image, and allocating a gradation curve so that a reference value of a pixel value within the ROI (for example, a maximum value or a median value) becomes a predetermined density has been proposed.

However, in the above-described scheme, since accessory information such as the imaged portion and the imaging direction of the radiation image and the age of the test substance is necessary, it is necessary for the accessory information of the radiation image to be input to the image processing device that performs image processing each time a radiation image is captured. Here, the accessory information is input by an operator who performs imaging selecting an imaging menu in the image processing device. For example, approximately 100 to 300 imaging menus are often used although the number of imaging menus varies depending on a facility. Accordingly, for the operator who performs imaging, work of selecting a desired imaging menu becomes very complicated, and mistyping easily occurs. Further, in order to perform optimum image processing, it is necessary to set optimum image processing parameters for each imaging menu, and an adjustment work for the setting also becomes very complicated. Meanwhile, by introducing a radiology information system (hereinafter referred to as an RIS), an imaging menu can be assigned to order information of the imaging, and thus, it is not necessary to perform work of inputting the imaging menu. However, in the case of a facility in which the RIS is not introduced, the operator needs to perform input of the imaging menu each time at the time of imaging.

In large hospitals, since there are image processing personnel, it is easy to make a modification when image quality of a radiation image cannot be satisfied. However, in small hospitals, since it is not easy to employ image processing personnel, modifying a radiation image to obtain image quality at the same level as obtained by image processing personnel becomes very difficult work. Thus, there is need for an image processing device capable of automatic conversion to an image suitable for diagnosis regardless of test substance or imaging conditions (a tube voltage, an amount of radiation, positioning, or the like).

In JP4844560B, a scheme of extracting a region of interest from a radiation image and converting a gradation of the radiation image so that a density of the extracted region becomes a desired density has been proposed. The scheme described in JP4844560B is a scheme of extracting a bone portion or a soft portion included in the radiation image as a region of interest, generating a weighted image by weighting the extracted region of interest, multiplying the weighted image by the radiation image to create a weighted histogram, evaluating the weighted histogram using a predetermined evaluation function, calculating a shift value of the histogram at which an evaluation value is maximized, and determining image processing conditions so that a predetermined processing result is obtained in a pixel value of the radiation image corresponding to a maximum value of the evaluation function used to obtain this shift value and, particularly, image processing conditions so that a pixel value corresponding to the shift value becomes a desired density. According to the scheme in JP4844560B, since the region of interest is extracted from an image without using accessory information of the image and the image processing conditions are determined for each image using the extracted region, it is possible to obtain a radiation image subjected to gradation processing without input of an imaging menu.

Incidentally, in diagnosis using a radiation image, it is important to recognize a change in the inside of a body by observing the image. For example, if inflammation is generated in a lung field, a portion thereof exhibits a low density (high luminance) in a radiation image. Further, when diagnosis of osteoporosis is performed, a portion thereof exhibits a high density (low luminance) in the radiation image. Therefore, in the diagnosis using a radiation image, it is important to perform image processing to reflect a change in a composition in a body in a change in the density of the image.

However, in the scheme described in JP4844560B, since a bone portion or a soft portion considered to be important is converted to have a predetermined density, when a tissue change such as inflammation occurs in a tissue of the bone portion or the soft portion considered to be important, the tissue change cannot be reflected in a change in the density of the radiation image.

Therefore, a scheme of performing gradation processing using a density of a region of which the density does not change even when the composition changes physically in the radiation image has been proposed (JP2000-079110A or the like). In the scheme described in JP2000-079110A, a thoracic region and a shoulder (clavicle) region are extracted as regions always maintaining the same density in a radiation image of a chest portion, and lesions of other regions are observed based on a representative value of this region.

SUMMARY OF THE INVENTION

Incidentally, even when observation of progress of a bone portion such as a fractured portion is performed in a radiation image of which a bone such as a limb bone is a subject, a composition of the bone portion changes physically due to curing of the fractured portion, or the like. Accordingly, it is necessary to perform gradation processing so that the change is reflected as a change in the density. However, in the scheme described in JP2000-079110A, since image processing is performed based on the density of the bone portion in the radiation image, a change in a composition of the bone portion cannot be reflected in the density in the case of the radiation image of which the bone portion is a diagnosis target.

The present invention has been made in view of the above-described circumstances, and an object of the present invention is to reflect a change in a state of a composition due to progression or curing of a disease, particularly, in a radiation image of which a bone portion is a diagnosis target, in an appropriately processed radiation image.

A radiation-image processing device according to the present invention is a radiation-image processing device that performs image processing including gradation processing on a radiation image acquired by irradiating a photographic subject with radiation, the radiation-image processing device including: determination means for determining that a diagnosis target is a bone portion of the photographic subject; region extraction means for extracting, as an anatomical region, a soft portion region corresponding to a soft portion of the photographic subject from the radiation image; feature amount calculation means for calculating a feature amount of a density of the radiation image based on the soft portion region; and image processing means for performing image processing including the gradation processing on the radiation image so that the feature amount becomes a target density.

In the radiation-image processing device according to the present invention, the region extraction means may be means for extracting the soft portion region near a center of the radiation image.

Further, in the radiation-image processing device according to the present invention, the region extraction means may be means for extracting the soft portion region in a region in a predetermined range from a gravity center position of a region of the photographic subject in the radiation image.

Further, in the radiation-image processing device according to the present invention, when the radiation image is acquired by performing imaging using an irradiation field stop, the region extraction means may be means for extracting the soft portion region included in an irradiation field region in the radiation image.

Further, in the radiation-image processing device according to the present invention, when an artifact is included in the radiation image, the feature amount calculation means may be means for calculating the feature amount based on a region other than a region of the artifact in the soft portion region.

Further, the radiation-image processing device according to the present invention may further include target density calculation means for calculating the target density based on the radiation image.

Further, in the radiation-image processing device according to the present invention, the photographic subject may be a limb bone, and particularly, a joint portion of the limb bone.

A radiation-image processing method according to the present invention is a radiation-image processing method of performing image processing including gradation processing on a radiation image acquired by irradiating a photographic subject with radiation, the radiation-image processing method including: extracting, as an anatomical region, a soft portion region corresponding to a soft portion of the photographic subject from the radiation image; calculating a feature amount of a density of the radiation image based on the soft portion region; and performing image processing including the gradation processing on the radiation image so that the feature amount becomes a target density.

A program for causing a computer to execute the radiation-image processing method according to the present invention may be provided.

According to the present invention, when image processing including gradation processing is performed on the radiation image, a diagnosis target is determined to be a bone portion of the subject, a soft portion region corresponding to a soft portion of the photographic subject is extracted as an anatomical region from the radiation image, a feature amount of a density of the radiation image is calculated based on the soft portion region, and image processing including the gradation processing is performed on the radiation image so that the feature amount becomes a target density. Therefore, when the bone portion is the diagnosis target, the feature amount can be calculated using a region in which the composition does not change with the elapse of time or a disease. Accordingly, a change in the composition of the bone portion due to progression or curing of a disease can be appropriately reflected in the processed radiation image.

DESCRIPTION OF THE PREFERRED EMBODIMENTS

Figure 1:
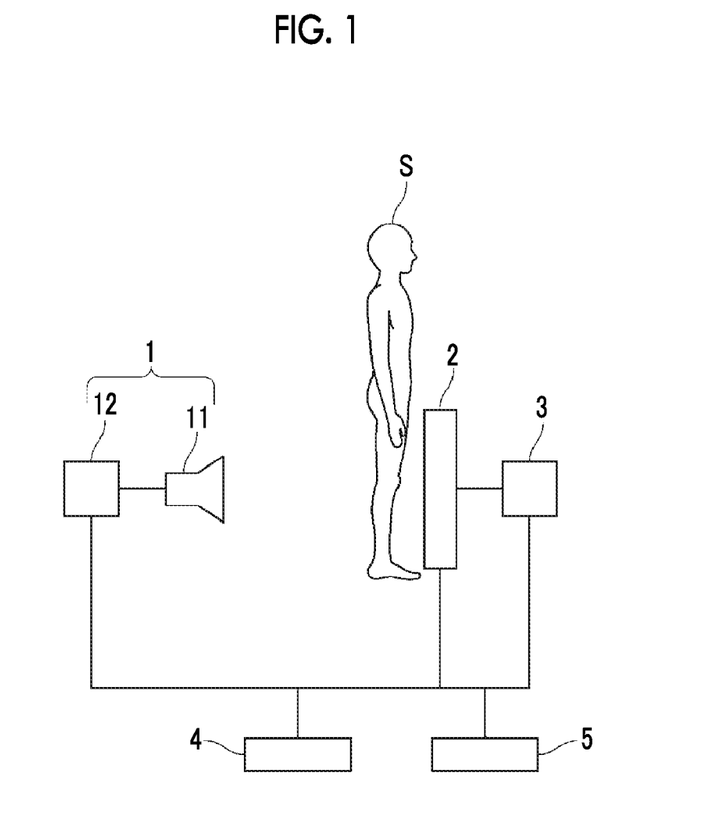
FIG. 1 is a schematic block diagram illustrating a configuration of a radiation image diagnosis system to which a radiation-image processing device according to an embodiment of the present invention is applied.

Hereinafter, embodiments of the present invention will be described with reference to the drawings. FIG. 1 is a schematic block diagram illustrating a configuration of a radiation image diagnosis system to which a radiation-image processing device is applied according to an embodiment of the present invention. As illustrated in FIG. 1, this radiation image diagnosis system includes a radiation generator 1, a radiation detector 2, a radiation-image processing device 3, an imaging control device 4, and an input unit 5. The radiation generator 1 and the radiation detector 2 are arranged to face each other with test substance S interposed therebetween. Further, the imaging control device 4 is connected to each of the radiation generator 1, the radiation detector 2, the radiation-image processing device 3, and the input unit 5. The radiation detector 2 is also connected to the radiation-image processing device 3. Further, in the description of this embodiment, a lower limb of the photographic subject S and, particularly, a joint of a knee are diagnosis targets.

The radiation generator 1 includes a radiation tube 11 that radiates radiation, and a high-voltage generator 12 that applies a tube voltage to the radiation tube 11, and can radiate the radiation to the photographic subject S under the control of the imaging control device 4. Setting of imaging conditions such as the tube voltage, a tube current, and a radiation time, or control of an operation based on the imaging conditions is performed by the imaging control device 4 based on the input from the input unit 5.

The radiation detector 2 accumulates radiation image information obtained from radiation transmitted through the photographic subject S as an electrostatic latent image, and detects a light transmittance distribution of the radiation as a radiation image by reading the accumulated electrostatic latent image. The radiation detector 2 may have any configuration in which radiation is detected and output as image information and may be, for example, a solid-state detector using a TFT scheme or a solid-state detector using a light reading scheme.

The radiation-image processing device 3 is a computer including a high-definition liquid crystal display that performs displaying of an image or the like, a keyboard or a mouse (that is, an input unit 5) that receives an input from an operator, and a main body including, for example, a CPU, a memory, a hard disk, and a communication interface, and has a function of performing various image processing including gradation processing on the radiation image.

The input unit 5 includes, for example, a keyboard, a mouse, and a touch panel type input unit, and is an interface that receives various inputs necessary for the radiation image diagnosis system, such as an imaging instruction, an image processing instruction, an imaging menu designation, or the like from the operator.

Figure 2:
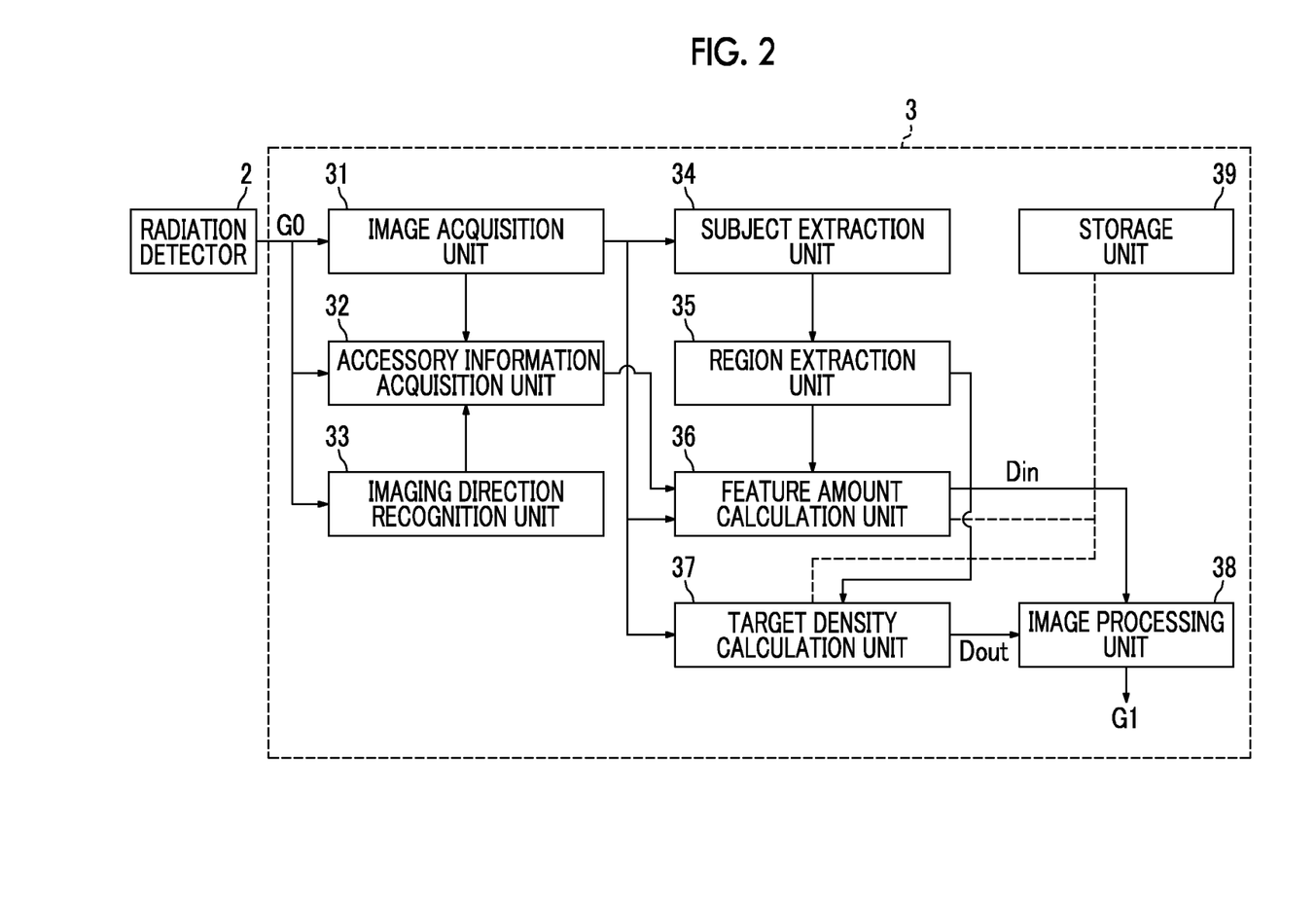
FIG. 2 is a schematic block diagram illustrating a configuration of the radiation-image processing device.

FIG. 2 is a schematic block diagram illustrating a configuration of the radiation-image processing device 3. As illustrated in FIG. 2, the radiation-image processing device 3 includes an image acquisition unit 31, an accessory information acquisition unit 32, an imaging direction recognition unit 33, a photographic subject extraction unit 34, a region extraction unit 35, a feature amount calculation unit 36, a target density calculation unit 37, an image processing unit 38, and a storage unit 39.

The image acquisition unit 31 acquires a radiation image G0 acquired by the radiation detector 2 as digital data.

Figure 3:
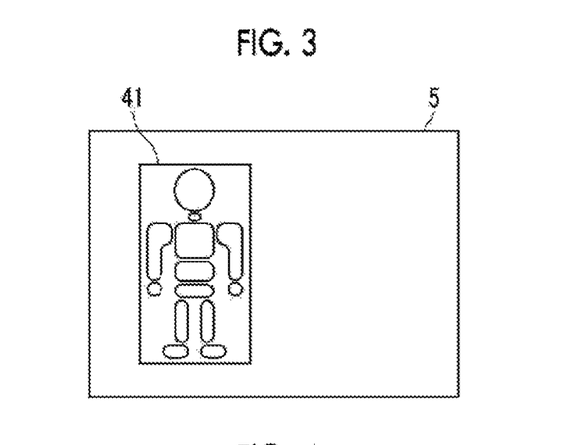
FIG. 3 is a diagram illustrating an interface displayed on an input unit with respect to an input of an imaged portion.

The accessory information acquisition unit 32 acquires accessory information H0 of the radiation image G0 such as an imaged portion and an imaging direction of the test substance S. Here, in this embodiment, the imaged portion of the accessory information H0 is acquired by the input unit 5 receiving an input of the accessory information H0 from the operator. FIG. 3 is a diagram illustrating an interface displayed in the input unit 5 with respect to an input of the imaged portion in the accessory information H0. As illustrated in FIG. 3, an image 41 simulating a human body is displayed on the input unit 5. In this image 41, respective portions of the human body such as a head portion, a neck portion, a chest portion, an abdomen portion, a waist portion, an upper limb, a lower limb, hands, and feet are separated and shown. The operator may input the imaged portion as the accessory information H0 by, for example, touching and selecting the imaged region in this image 41. The imaging direction is acquired from the imaging direction recognition unit 33 to be described below. In this embodiment, while both of the imaged portion and the imaging direction are acquired as the accessory information H0, any one of the imaged portion and the imaging direction may be acquired as the accessory information H0.

The imaged portion may be acquired by image-analyzing the radiation image G0. For example, learning may be performed using the radiation image of each imaged portion as teacher data through machine learning such as an Adaboost scheme, and an imaging portion discriminator may be provided in the accessory information acquisition unit 32. Using this discriminator, the radiation image G0 may be analyzed and the imaging portion may be acquired as the accessory information H0.

The imaging direction recognition unit 33 acquires the imaging direction of the radiation image G0 by image-analyzing the radiation image G0. For example, learning is performed for various imaged portions through machine learning such as an Adaboost scheme using, as teacher data, radiation images captured in front, a side, and an axis position (body-axis direction), and an imaging portion discriminator is provided in the accessory information acquisition unit 32. Using this discriminator, the radiation image G0 is analyzed and the imaging direction is recognized. The recognized imaging direction is input as a portion of the accessory information H0 to the accessory information acquisition unit 32 so that the imaging direction is used for, for example, calculation of a target density to be described below.

The photographic subject extraction unit 34 extracts a photographic subject region included in the radiation image G0. As a scheme of extracting the photographic subject region, any known scheme, such as a scheme for performing a binarization process on the radiation image G0 to divide the radiation image G0 into a photographic subject region obtained by irradiating the radiation detector 2 with radiation transmitted through the photographic subject S in the radiation image G0, and a direct transmission region obtained by directly irradiating the radiation detector 2 with radiation, for example, as described in JP2001-145614A, may be used.

The region extraction unit 35 extracts a bone portion region and a soft portion region from the photographic subject region that the photographic subject extraction unit 34 extracts from the radiation image G0. Here, the bone portion region refers to a region on the radiation image G0 obtained by irradiating the radiation detector 2 with radiation transmitted through a bone of the photographic subject S, and the soft portion region refers to a region on the radiation image G0 obtained by irradiating the radiation detector 2 with radiation transmitted through a tissue or an organ (soft portion) other than the bone of the photographic subject S. In general, the bone portion has a low density (high luminance) since an amount of radiation transmission is small, and the soft portion has a high density (low luminance) since the amount of radiation transmission is large, but the amount of radiation transmission is a smaller than that of a direct transmission portion.

Therefore, as a scheme of extracting the bone portion region in the region extraction unit 35, known schemes such as a scheme of extracting, as a bone portion region, a region having a density equal to or lower than a reference density from a photographic subject region using the fact that a density of an image of the bone portion region is lower (luminance is higher) than that of another region, that is, the soft portion region, and a scheme of extracting a contour of a bone portion described in JP2010-253243A can be used. Further, as described in JP4844560B, the bone portion region may be extracted based on a bone portion edge or the like included in a photographic subject region using various image processing for performing skeletonization, such as top hat processing or skeleton processing, or an edge detection scheme using a Laplacian filter, a Sobel filter, or the like may be used. Further, when a plurality of schemes are used, results of the plurality of schemes may be summed according to predetermined weighting. In this case, a scheme of determining a method of summation according to a neural network may be used. The region extraction unit 35 removes the bone portion region extracted as described above from the photographic subject region to extract the soft portion region.

The feature amount calculation unit 36 calculates, as the feature amount Din, a pixel value serving as a reference of the gradation processing from the radiation image G0. The pixel value serving as a reference refers to a pixel value converted to a target density Dout to be described below by performing the gradation processing. Hereinafter, calculation of the feature amount Din will be described. In this embodiment, the feature amount calculation unit 36 first determines a region used for calculation of the feature amount Din (hereinafter referred to as a use region) to be any one of the bone portion region and the soft portion region. The use region is determined to be a non-diagnosis target region that is not a diagnosis target, rather than a diagnosis target region that is a diagnosis target, based on the accessory information H0 acquired by the accessory information acquisition unit 32. The feature amount calculation unit 36 has a function of determination means.

Here, since the radiation image G0 in which the imaged portion is a knee joint, a thigh, or the like is often intended for diagnosis of bone fracture, osteoporosis diagnosis, or the like, and progress of a state of the bone portion is mainly observed for diagnosis, the bone portion region becomes the diagnosis target region. In this case, when the bone portion region is determined to be the use region, the feature amount Din is determined using a region of which the state, that is, the density is changed due to progression or curing of a disease. Accordingly, when the feature amount Din is converted to the target density Dout as described below, a change in a composition of the bone portion due to progression or curing of a disease cannot be accurately reproduced on the processed radiation image. Therefore, when the bone portion is the diagnosis target region, the soft portion region that is a non-diagnosis target region in which there is no change in density due to progression or curing of a disease is determined to be the use region. Therefore, when the bone portion is the diagnosis target region, the soft portion region that is a non-diagnosis target region, of which the density is not changed by progression or curing of a disease, is determined to be the use region.

On the other hand, when a soft portion such as an Achilles tendon is desired to be observed, the soft portion is a diagnosis target region. In such a case, the bone portion region that is a non-diagnosis target region, of which the density is not changed by progression or curing of a disease, is determined to be the use region.

Here, in this embodiment, a table T1 in which various imaged portions and the diagnosis target region are associated with each other is generated in advance and stored in the storage unit 39, the diagnosis target region is determined from the information on the imaged portion by referring to this table T1, and a non-diagnosis target region different from the determined diagnosis target region is determined to be a region used for calculation of the feature amount Din. In this embodiment, since the imaged portion is a lower limb, the bone portion is determined to be the diagnosis target region. As a result, the use region is determined to be the soft portion region.

In this embodiment, a table T1' in which the various imaged portions and the use region are associated with each other may be generated in advance and stored in the storage unit 39, and the region used for calculation of the feature amount Din may be determined from information on the imaged portion by referring to the table T1'.

Any one of the bone portion region and the soft portion region to be used may be determined according to a type of clinical department. For example, in the case of the radiation image G0 in which the imaged region is the chest portion, a state of the lung field is observed and diagnosis is performed in internal medicine, whereas a state of the rib is observed and diagnosis is performed in orthopedics. Therefore, in the radiation image G0 of the same imaged portion, if clinical departments are different from each other, the diagnosis target regions are different from each other. Here, when a state of the lung field is desired to be observed and the soft portion region is determined to be the use region, a change in a state in the lung field cannot be accurately reproduced on the processed radiation image. On the other hand, when a state of the bone portion is desired to be observed and the bone portion region is determined to be the use region, a state of a change in the rib cannot be accurately reproduced on the processed radiation image.

Therefore, the accessory information acquisition unit 32 acquires a type of clinical department as the accessory information H0 and may determine the use region according to the imaged portion and the type of clinical department. Specifically, in the radiation image G0 in which the imaged portion is a chest portion, if the clinical department is internal medicine, the bone portion region may be determined to be the use region, and if the clinical department is orthopedics, the soft portion region may be determined to be the use region. Accordingly, for radiation images of the same chest portion, a state of the lung field can be correctly observed in internal medicine and a state of the rib can be correctly observed in orthopedics. In this embodiment, since the diagnosis target is a lower limb, the clinical department is highly likely to be orthopedics. Therefore, the diagnosis target is determined to be the bone portion. As a result, the use region is determined to be the soft portion region.

Further, it is understood that the diagnosis target region may be switched to either the bone portion or the soft portion by designation of a user.

The feature amount calculation unit 36 generates a histogram of pixel values in the determined use region (that is, soft portion region), and calculates the feature amount Din based on the histogram. As the feature amounts Din, an average value or a median value of the histogram, a value (for example, 20%) of several percent from, for example, a highest density of the histogram, or the like may be used.

Figure 4:
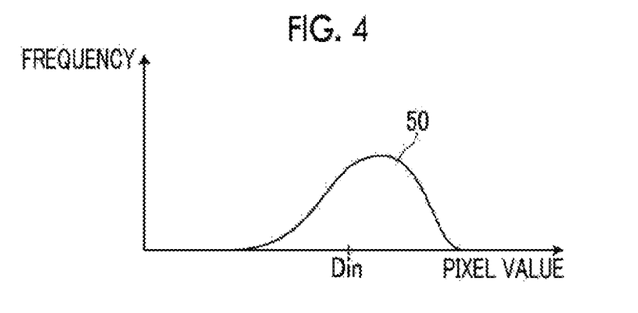
FIG. 4 is a diagram illustrating a histogram of a use region and a calculated feature amount Din.

FIG. 4 is a diagram illustrating the histogram of the use region and the calculated feature amount Din. In FIG. 4, the median value of the histogram 50 of the use region is calculated as the feature amount Din.

Any one of these values to be used may be determined based on the accessory information H0. For example, a table T2 in which various imaged portions and various values of the histogram are associated with each other may be generated in advance and stored in the storage unit 39, any one of the values of the histogram to be used may be determined by referring to the table T2 based on information on the imaged portion included in the accessory information H0, and the feature amount Din may be calculated.

Figure 5:
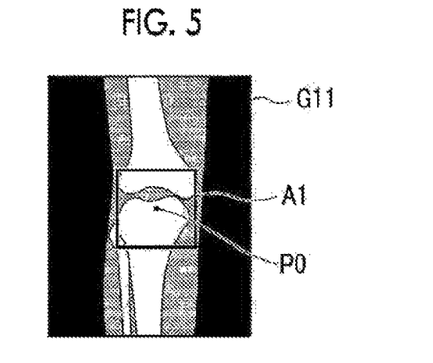
FIG. 5 is a diagram illustrating a radiation image of a knee joint.

Incidentally, for example, when the imaged portion is a lower limb, and particularly, a knee, positioning is performed so that the knee is located at a center of the radiation image, and imaging is performed. Here, since a thickness of a soft portion region in a portion of the knee is substantially constant, and a change in the thickness is small according to a body size of the photographic subject S, the feature amounts Din can be stably calculated using the soft portion region around the knee. Therefore, when the feature amount Din is calculated, the use region may be limited so that only the soft portion region in a region near a central position of the radiation image is used. In particular, since a center of the radiation image often coincides with the gravity center position of the photographic subject region, the gravity center position of the photographic subject region may be calculated, the usage region may be limited so that only the soft portion region within a predetermined range from the gravity center position is used, a histogram is calculated using only pixel values in the limited use region, and the feature amount Din may be calculated. Here, the gravity center position of the photographic subject region is in a position close to a center of the radiation image G0. Therefore, as illustrated in FIG. 5, in the radiation image G11 acquired by performing imaging so that the knee is located at the center, the use region is limited to a region A1 in a predetermined range from the gravity center position P0 of the photographic subject region, such that the use region for calculating the feature amount Din can be limited to the soft portion region around the knee. Accordingly, the feature amount Din can be stably calculated regardless of the change in the composition of the bone portion region.

It is preferable for a distance from the gravity center position to be changed according to the imaged portion included in the accessory information H0. In this case, a table T3 in which various imaged portions and the distance from the gravity center position are associated with each other may be generated in advance and stored in the storage unit 39, the distance from the gravity center position may be determined by referring to the table T3 based on information on the imaged portion included in the accessory information H0, and the feature amount Din can be calculated.

Figure 6:
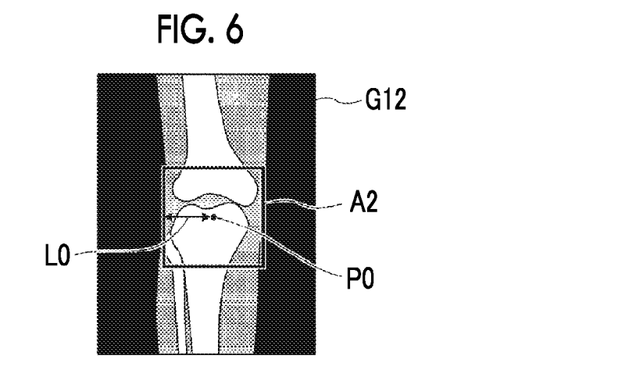
FIG. 6 is a diagram illustrating a radiation image of the knee joint.

Further, a shortest distance from the gravity center position of the photographic subject region to a region outside the photographic subject may be calculated, and the histogram may be calculated using only the pixel values of the bone portion region and soft portion region within a distance based on the shortest distance. For example, as illustrated in FIG. 6, in a radiation image G12 of a knee joint, a shortest distance L0 from the gravity center position P0 to the region outside the photographic subject may be obtained and a square region A2 in which one side is 2L0 may be limited to the use region. When imaging is performed using an irradiation field stop, the gravity center position of the irradiation field region may be used as the gravity center position of the photographic subject region. Accordingly, the feature amount Din can be calculated from the soft portion region in the irradiation field region.

Further, an image of a fastener for fixing a target region at the time of imaging or an artifact such as an artificial joint may be included in the radiation image G0, but the artifact appears as a region with a low density (high luminance) in the radiation image. Accordingly, when the artifact is included in the use region, the histogram swings to a low density side, and thus, the feature amount Din cannot be stably calculated despite the imaged portion being the same. Therefore, a region that is low in density is extracted as a region of the artifact from the photographic subject region. When the artifact is included in the use region, the artifact, or the artifact and a region around the artifact is removed from the use region. Accordingly, it is possible to stably calculate the feature amount Din not affected by the artifact.

Figure 7:
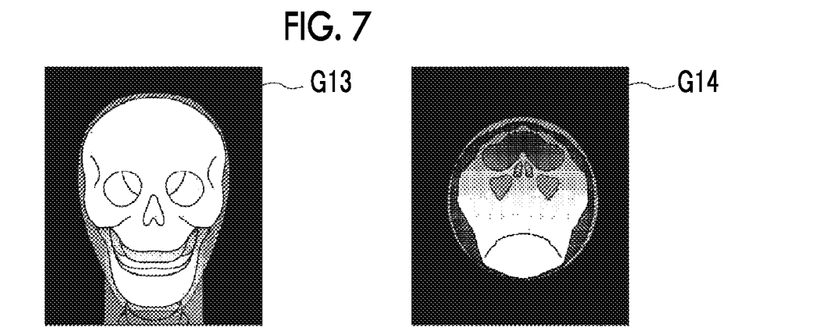
FIG. 7 is a diagram illustrating a radiation image of a head portion.

The target density calculation unit 37 calculates a target density Dout that is a target density of the feature amount Din. Hereinafter, calculation of the target density Dout will be described. FIG. 7 is a view illustrating a radiation image of the front of a head portion and a radiation image of an axis position. As illustrated in FIG. 7, in a radiation image G13 in which an imaging direction is from the front, since a thickness of the bone portion region over a substantially entire photographic subject region is substantially uniform, a density of the entire photographic subject region is generally relatively low, and a density of an orbital region is relatively low. In contrast, in a radiation image G14 in which the imaging direction is an axis position, a thickness of the bone portion region is not uniform in each pixel, there is a low density region and a high density region in the bone portion region, and a density of the orbital region becomes relatively high. Thus, when the gradation processing is performed using the same target density Dout due to the imaged portion, optimal image quality of the processed radiation image cannot be achieved according to the imaging direction since Din calculated from the bone portion region and a density difference of an orbit are different from each other.

Therefore, in this embodiment, the target density calculation unit 37 determines one of a front, a side, and an axis position (body-axis direction) of the photographic subject S from which the radiation image G0 has been captured based on information on the imaging direction recognized by the imaging direction recognition unit 33, and calculates the target density Dout according to the imaging direction. Here, in this embodiment, a table T4 in which various imaging directions and the target density Dout are associated with each other is stored in the storage unit 39, and the target density calculation unit 37 calculates the target density Dout from the information on imaging direction by referring to the table T4.

Further, the target density calculation unit 37 may calculate the target density Dout based on a shape of the photographic subject region extracted by the photographic subject extraction unit 34. For example, when the imaged region is the head portion, the shape of the photographic subject region is close to a circle. That is, when a degree of circularity is higher, the image is likely to have been captured from the axis position direction. Therefore, the degree of circularity of the photographic subject region may be calculated, a table T5 in which the degree of circularity of the photographic subject region and the target density Dout are associated with each other may be stored in the storage unit 39, and the target density Dout may be calculated from the shape of the photographic subject region by referring to the table T5.

For other imaged portions other than the head portion, the shape of the photographic subject S is characterized by the imaging direction. Therefore, a degree of a shape indicating a degree of a certain shape that the photographic subject region has may be calculated, a table in which the degree of the shape of the photographic subject region and the target density Dout are associated with each other may be stored in the storage unit 39, and the target density Dout may be calculated from the shape of the photographic subject region by referring to this table.

Further, the target density Dout may be calculated based on the distribution of the bone portion region extracted by the region extraction unit 35. For example, in the case of the radiation image G0 in which the imaged portion is a head portion, the bone portion region is distributed over substantially the entire photographic subject region in the radiation image G13 captured from the front, whereas the thicker bone portion region is widely distributed on the lower side of the photographic subject region in the case of the radiation image G14 captured from the axis position, as illustrated in FIG. 7. Therefore, a table T6 in which a distribution state of various bone portion regions in the photographic subject region and the target density Dout for each imaged portion are associated with each other may be stored in the storage unit 39, and the target density Dout may be calculated from the distribution of the bone portion region by referring to the table T6.

Further, in the case of the radiation image G0 in which the imaged portion is a head portion, a ratio of an area of the bone portion region exhibiting a low density to an area of the photographic subject region increases as illustrated in FIG. 7. Therefore, the imaging direction can be specified using the ratio of an area of the bone portion region exhibiting a low density to an area of the photographic subject region. Accordingly, the target density Dout may be calculated based on the ratio of an area of the bone portion region exhibiting a low density to an area of the photographic subject region. In this case, a table T7 in which various ratios of the area of the bone portion region to the area of the photographic subject region and the target density Dout are associated with each other for each imaged portion may be stored in the storage unit 39, and the target density Dout may also be calculated from the ratio of the area of the bone portion region to the area of the photographic subject region by referring to the table T7.

Figure 8:
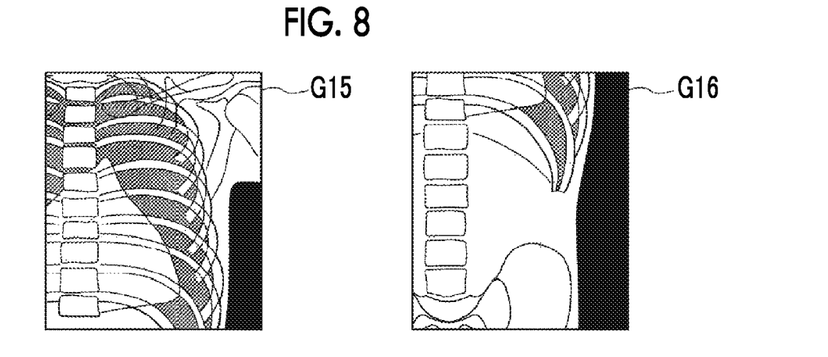
FIG. 8 is a diagram illustrating a radiation image of a chest portion.

Further, when the imaged portion is a chest, the region extraction unit 35 may extract a lung field region as the anatomical region, and calculate the target density Dout based on the distribution of the lung field region. FIG. 8 is a diagram illustrating a radiation image in which imaged portion is the chest and, particularly, a radiation image of an upper rib and a radiation image of a lower rib. As illustrated in FIG. 8, in the radiation image G15 in which the imaging region is the upper rib, the lung field region is distributed in an entire vertical direction of the photographic subject region. On the other hand, in the radiation image G16 in which the imaged portion is the lower rib, the lung field region is distributed only on the upper side of the photographic subject region, and accordingly, when the imaged portion is the lower rib, a large amount of a tissue of an abdomen is included as compared with the case in which the imaged portion is the upper rib. As a result, a density of the photographic subject region becomes low as a whole. Therefore, an optimal density and contrast of the rib in the processed radiation image cannot be achieved according to the imaged portion by performing the gradation processing using the same target density Dout when the upper rib and the lower rib are the same imaged portions. Therefore, a table T8 in which distributions of various lung field regions and the target density Dout are associated with each other may be stored in the storage unit 39, and the target density Dout may be calculated from the distribution of the lung field region by referring to the table T8. For the extraction of the lung field region, any known scheme such as a scheme of binarizing the soft portion region into an air region and a soft portion tissue region and extracting the lung field region may be used.

Further, in the radiation image of the upper rib, the lung field region exists throughout in the vertical direction of the image, whereas in the radiation image of the lower rib, the lung field region only in an upper portion of the image. Therefore, it can be recognized whether the imaged portion of the radiation image is the upper rib or the lower rib from the distribution of the lung field region. Therefore, a table T9 in which the imaged portion and the target density Dout are associated with each other may be stored in the storage unit 39, and the target density Dout may be calculated from the imaged portion recognized based on the distribution of the lung field region by referring to the table T9.

Here, in this embodiment, the target density Dout may be acquired through the calculation described above or a predetermined value may be used if a change in the composition in the bone portion can be appropriately reproduced using the change in the density of the radiation image.

The calculation of the target density Dout is not limited to the above scheme, and any known scheme may be used. Further, the various schemes may be combined to calculate the target density Dout.

Figure 9:
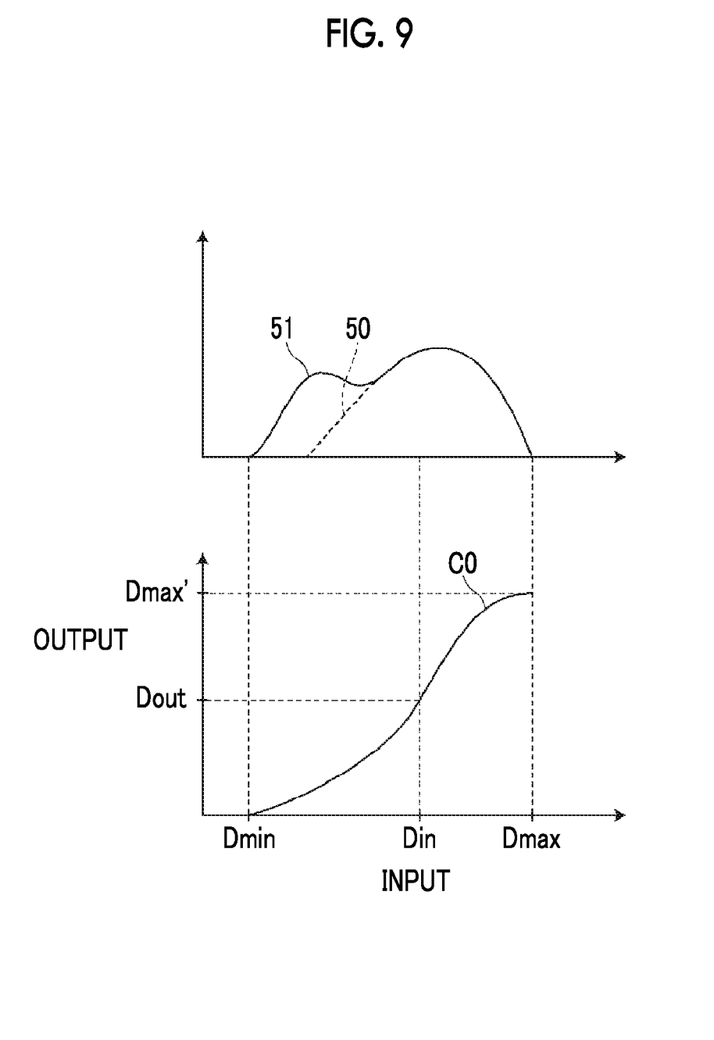
FIG. 9 is a diagram illustrating setting of a gradation curve.

The image processing unit 38 sets the gradation curve so that the feature amount Din becomes the target density Dout. FIG. 9 is a diagram illustrating setting of the gradation curve. In FIG. 9, a histogram 51 of the photographic subject region is indicated by a solid line, and a histogram 50 of a use region (the soft portion region herein) used to calculate the feature amount Din is indicated by a dashed line. First, the image processing unit 38 determines a minimum density Dmin and a maximum density Dmax of the photographic subject region. The minimum density Dmin and the maximum density Dmax are a minimum value and a maximum value of a horizontal axis (that is, pixel value) of the histogram 51 of the photographic subject region. The image processing unit 38 sets a gradation curve C0 so that the feature amount Din calculated by the feature amount calculation unit 36 as illustrated in FIG. 5 becomes the target density Dout calculated by the target density calculation unit 37 and the maximum density Dmax becomes a maximum density Dmax' of an output device (for example, display device) of the processed radiation image G1.

The image processing unit 38 converts the gradation of the radiation image G0 using the set gradation curve. Further, the image processing unit 38 performs other image processing such as frequency processing or a graininess suppression process to acquire the processed radiation image G1.

Figure 10:
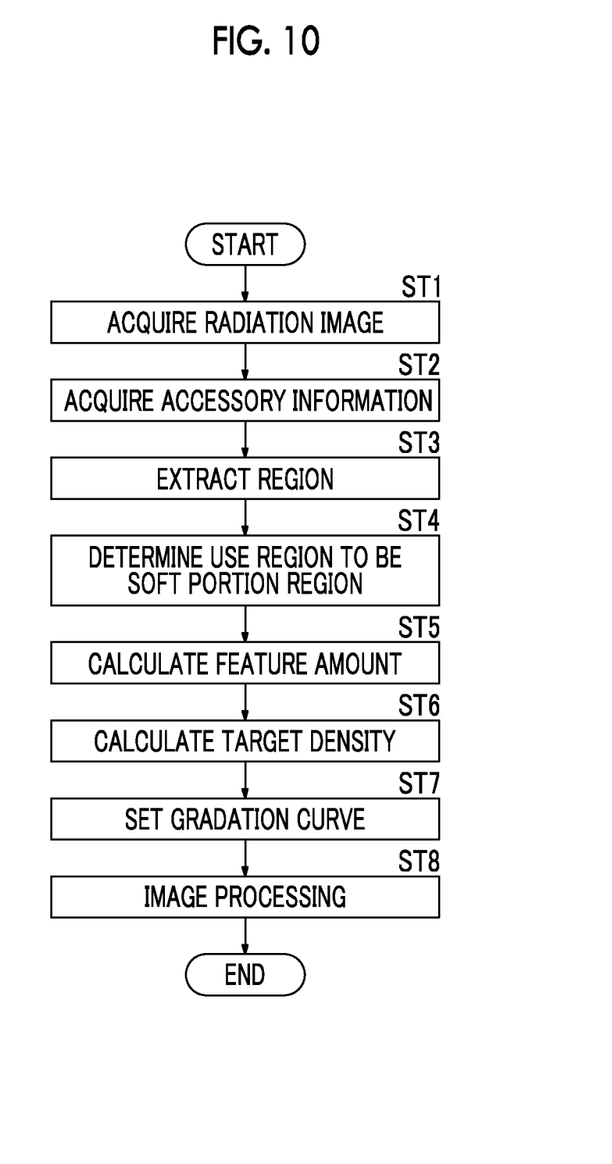
FIG. 10 is a flowchart illustrating a process performed in this embodiment.

Next, a process performed in this embodiment will be described. FIG. 10 is a flowchart illustrating a process performed in this embodiment. Imaging of the photographic subject S is assumed to have been completed. First, the image acquisition unit 31 acquires the radiation image P0 from the radiation detector 2 (step ST1), and the accessory information acquisition unit 32 acquires the accessory information H0 of the radiation image G0 (step ST2). Then, the photographic subject extraction unit 34 extracts the photographic subject region included in the radiation image G0, and the region extraction unit 35 extracts the bone portion region and the soft portion region from the photographic subject region (region extraction; step ST3). The feature amount calculation unit 36 determines the use region to be used for calculation of the feature amount Din to be the soft portion region (step ST4), and calculates the feature amount Din from the soft portion region (step ST5). Further, the target density calculation unit 37 calculates a target density Dout for converting the feature amount Din (step ST6), and the image processing unit 38 sets a gradation curve C0 so that the feature amount Din becomes the target density Dout (step ST7). Further, the image processing unit 38 performs image processing including gradation processing using the gradation curve C0 on the radiation image G0 to acquire the processed radiation image G1 (step ST8), and ends the process.

Thus, in this embodiment, the feature amount Din of the radiation image G0 is calculated based on the soft portion region in the radiation image G0, and the gradation processing is performed on the radiation image G0 so that the feature amount Din becomes the target density Dout. Therefore, when the bone portion is a diagnosis target, the feature amount Din can be calculated using a region of which the state does not change with the elapse of time or a disease. Accordingly, a change in the composition of the diagnosis target region due to progression or curing of a disease can be appropriately reflected in the processed radiation image G1.

Further, by setting the target density Dout based on the radiation image G0, an appropriate target density Dout can be set according to the radiation image G0 without finely setting the imaging menu, and accordingly, image quality of the processed radiation image G1 and, particularly, the density and the contrast can be optimized while reducing the number of imaging menus to be set.

Further, by recognizing the imaging direction based on the radiation image G0 and calculating the target density based on the recognized imaging direction, it is possible to omit the setting of the imaging menu regarding the imaging direction.

Further, by extracting the anatomical region such as the bone portion region, the soft portion region, and the lung field region from the radiation image G0 and calculating the target density Dout based on at least one of the position, the size, and the distribution of the anatomical region, it is possible to omit the setting of the imaging menu regarding at least one of the position, the size, and the distribution of the anatomical region.

While the lower limb of the photographic subject S is the diagnosis target in the above embodiment, the upper limb may be the diagnosis target. Further, any portion of the bone portion may be the diagnosis target.

While the feature amount calculation unit 36 determines the use region used for calculation of the feature amount Din in the above-described embodiment, the image quality of the processed radiation image G1 may not be stable when the feature amount Din is calculated from the determined use region. For example, since a radiation image of a terminal portion of a human body, such as a finger, a hand or a foot, is captured for diagnosing in a bone portion, the diagnosis region is the bone portion. Accordingly, according to this embodiment, a region used for calculation of the feature amount Din is determined to be the soft portion region that is non-diagnosis region. However, since a range of the soft portion region in the terminal portion is narrow, when the feature amount Din is calculated using a histogram of the soft portion region, the feature amount Din is not stable. As a result, the image quality of the processed radiation image G1 is not stable.

Therefore, it may be determined whether an area of the photographic subject extracted by the photographic subject extraction unit 34 is below a certain percentage of the radiation image G0, and if this determination is positive, the region used for calculation of the feature amount Din may be determined to be the bone portion region. Further, any one of the bone portion region and the soft portion region to be used for calculation of the feature amount Din may be determined depending on areas of the bone portion region and the soft portion region. For example, when the bone portion is the diagnosis target region, the region used for calculation of the feature amount Din may be determined to be the soft portion region. However, when the soft portion region has a smaller area, the region used for calculation of the feature amount Din may be switched to the bone portion region. Further, when portion recognition of the photographic subject region is performed and the recognized portion is the terminal portion such as a finger, a hand or a foot, the region used for calculation of the feature amount Din may be determined to be the bone portion region.

Further, while the bone portion region and the soft portion region may be extracted from the photographic subject region so as to determine the region used for calculation of the feature amount Din in the above-described embodiment, there is no bone portion region when the imaged portion is a breast. Therefore, in the radiation image G0 in which the imaged portion is a breast, the photographic subject region may be divided into a mammary gland region and a fat region. Here, in the case of the breast, since the diagnosis target region is the mammary gland region, the region used for calculation of the feature amount Din may be the fat region.

While the non-diagnosis target region among the bone portion region and the soft portion region has been determined to be the region used for calculation of the feature amount Din in the above-described embodiment, the present invention is not limited thereto, and the diagnosis target region serving as a diagnosis target may be determined to be the region used for calculation of the feature amount Din.

Further, while the radiation image of the photographic subject S has been acquired using the radiation detector 2 in the above-described embodiment, a portion of radiation energy may be accumulated through irradiation of the radiation, and then the radiation image may be acquired using a stimulable phosphor sheet using stimulable fluorescent light that emits stimulated emission light according to the accumulated radiation energy through irradiation of excitation light such as visible light or laser light. When a stimulable phosphor sheet is used, the stimulable phosphor sheet is irradiated with the radiation transmitted through the photographic subject such that radiation image information is accumulated and recorded once, the stimulable phosphor sheet is irradiated with excitation light such that stimulated emission light is generated, and the stimulated emission light is photoelectrically converted so as to acquire a radiation image.

Hereinafter, operations and effects of dependent claims of the present invention will be described.

In a region near a center of the image, a thickness of the soft portion is stable in the same subject. Therefore, by extracting the soft portion region near the center of the radiation image, the feature amount can be stably calculated even when a composition of the bone portion is changed, and accordingly, the image quality of the processed radiation image acquired through gradation processing can be more suitable.

Further, when imaging is performed using an irradiation field stop, a portion that is a diagnosis target is included near a center of the radiation image. Therefore, when the radiation image is acquired by performing imaging using the radiation field stop, the radiation field region is extracted from the radiation image and the soft portion region included in the radiation field region is extracted, such that the soft portion region near the center of the radiation image can be reliably extracted. Therefore, since the feature amount can be calculated more stably, the image quality of the processed radiation image acquired through gradation processing can be more suitable.

By recognizing a region of an artifact included in the radiation image and calculating the feature amount based on a region other than the region of the artifact in the soft portion region, it is possible to more stably calculate the feature amount without any influence of the region of the artifact. Therefore, the image quality of the processed radiation image acquired through gradation processing can be more suitable.

Further, by calculating the target density based on the radiation image, an appropriate target density can be set according to the radiation image, and accordingly, the image quality of the radiation image acquired through processing can be optimized while reducing the number of imaging menus to be set.

What is claimed is:

1. A radiation-image processing device that performs image processing including gradation processing on a radiation image acquired by irradiating a photographic subject with radiation, the radiation-image processing device comprising:
   determination unit for determining that a diagnosis target is a bone portion of the photographic subject;
   region extraction unit for extracting a soft portion region, which is a non-diagnosis target region, of which a density is not changed by progression or curing of a disease, corresponding to a soft portion of the photographic subject from the radiation image;
   feature amount calculation unit for calculating a feature amount of the density of the non-diagnosis target region in the radiation image based on the soft portion region; and
   image processing unit for performing image processing including the gradation processing on the radiation image so that the feature amount of the non-diagnosis target region becomes a target density.

2. The radiation-image processing device according to claim 1,
   wherein the region extraction unit extracts the soft portion region near a center of the radiation image.

3. The radiation-image processing device according to claim 2,
   wherein the region extraction unit extracts the soft portion region in a region in a predetermined range from a gravity center position of a region of the photographic subject in the radiation image.

4. The radiation-image processing device according to claim 1,
   wherein when the radiation image is acquired by performing imaging using an irradiation field stop, the region extraction unit extracts the soft portion region included in an irradiation field region in the radiation image.

5. The radiation-image processing device according to claim 1,
   wherein when an artifact is included in the radiation image, the feature amount calculation unit calculates the feature amount based on a region other than a region of the artifact in the soft portion region.

6. The radiation-image processing device according to claim 1, further comprising:
   target density calculation unit for calculating the target density based on the radiation image.

7. The radiation-image processing device according to claim 1,
   wherein the photographic subject is a limb bone.

8. The radiation-image processing device according to claim 7,
   wherein the photographic subject is a joint portion of the limb bone.

9. A radiation-image processing method of performing image processing including gradation processing on a radiation image acquired by irradiating a photographic subject with radiation, the radiation-image processing method comprising:
   determining that a diagnosis target is a bone portion of the photographic subject;
   extracting a soft portion region, which is a non-diagnosis target region, of which a density is not changed by progression or curing of a disease, corresponding to a soft portion of the photographic subject from the radiation image;
   calculating a feature amount of the density of the non-diagnostic target region in the radiation image based on the soft portion region; and
   performing image processing including the gradation processing on the radiation image so that the feature amount of the non-diagnosis target region becomes a target density.

10. A non-transitory recording medium having stored therein a program that causes a computer to perform a radiation-image processing method of performing image processing including gradation processing on a radiation image acquired by irradiating a photographic subject with radiation, the program causing the computer to execute the procedures of:
   determining that a diagnosis target is a bone portion of the photographic subject;
   extracting a soft portion region, which is a non-diagnosis target region, of which a density is not changed by progression or curing of a disease, corresponding to a soft portion of the photographic subject from the radiation image;
   calculating a feature amount of the density of the non-diagnosis target region in the radiation image based on the soft portion region; and
   performing image processing including the gradation processing on the radiation image so that the feature amount of the non-diagnosis target region becomes a target density.

* * * * *